(12) United States Patent
Hyatt et al.

(10) Patent No.: US 11,938,643 B2
(45) Date of Patent: Mar. 26, 2024

(54) DEVELOPABLE AND COLLAPSABLE EXTERNAL CUTTING OR GRIPPING MECHANISM

(71) Applicant: Brigham Young University, Provo, UT (US)

(72) Inventors: Lance Hyatt, Provo, UT (US); Jacob Sheffield, Provo, UT (US); Kendall Hal Seymour, Springville, UT (US); Scott Cunnington, Provo, UT (US); Spencer Magleby, Provo, UT (US); Larry L. Howell, Orem, UT (US)

(73) Assignee: Brigham Young University, Provo, UT (US)

( * ) Notice: Subject to any disclaimer, the term of this patent is extended or adjusted under 35 U.S.C. 154(b) by 569 days.

(21) Appl. No.: 17/277,014

(22) PCT Filed: Sep. 18, 2019

(86) PCT No.: PCT/US2019/051727
§ 371 (c)(1),
(2) Date: Mar. 17, 2021

(87) PCT Pub. No.: WO2020/061190
PCT Pub. Date: Mar. 26, 2020

(65) Prior Publication Data
US 2022/0032485 A1 Feb. 3, 2022

Related U.S. Application Data

(60) Provisional application No. 62/732,903, filed on Sep. 18, 2018.

(51) Int. Cl.
B26B 27/00 (2006.01)
B23D 21/14 (2006.01)
(Continued)

(52) U.S. Cl.
CPC .............. *B26B 27/00* (2013.01); *B23D 21/14* (2013.01); *B23D 21/145* (2013.01); *E02D 9/04* (2013.01); *A61B 17/295* (2013.01)

(58) Field of Classification Search
CPC ... Y10T 83/384; Y10T 83/385; Y10T 83/386; B26B 27/00; A61B 17/295; E02D 9/005; E02D 9/04; B23D 21/14; B23D 21/145
See application file for complete search history.

(56) References Cited

U.S. PATENT DOCUMENTS 3,234,826 A * 2/1966 Gill ........................ B23D 21/14
144/205
3,630,105 A 12/1971 Rider
(Continued)

FOREIGN PATENT DOCUMENTS

JP  H04507363 A  12/1992
WO  2014027548 A1  2/2014
(Continued)

OTHER PUBLICATIONS

Nelson, et al., "Developable Mechanisms on Developable Surfaces," Brigham Young University disclosure 2018-032 (2018).
(Continued)

*Primary Examiner* — Phong H Nguyen
(74) *Attorney, Agent, or Firm* — Dorsey & Whitney LLP

(57) ABSTRACT

A hollow rod developable actuator tool including a cylinder defining the outer circumference of the hollow rod, a first tool mechanism, and a second tool mechanism. The hollow rod developable actuator tool transitions from a first closed state wherein the first tool mechanism and second tool mechanism are contained entirely within the outer circumference of the hollow rod to a second open state wherein the first tool mechanism and second tool mechanism extent outside the outer circumference of the hollow rod.

20 Claims, 7 Drawing Sheets

(51) Int. Cl.
*E02D 9/04* (2006.01)
*A61B 17/295* (2006.01)

(56) References Cited

U.S. PATENT DOCUMENTS

| | | | |
|---|---|---|---|
| 4,327,609 A | 5/1982 | Resch | |
| 4,524,511 A * | 6/1985 | Montiero | B23D 21/14 30/108 |
| 5,010,797 A | 4/1991 | Stepan | |
| 5,509,923 A | 4/1996 | Middleman et al. | |
| 6,215,081 B1 | 4/2001 | Jensen et al. | |
| 2005/0251167 A1 | 11/2005 | Voegele et al. | |
| 2008/0234725 A1 | 9/2008 | Griffiths et al. | |
| 2009/0018565 A1 | 1/2009 | To et al. | |
| 2013/0233139 A1 * | 9/2013 | Trudeau | B23D 21/14 83/191 |
| 2016/0051127 A1 | 2/2016 | Yoshimura | |
| 2016/0051274 A1 | 2/2016 | Howell et al. | |
| 2017/0354470 A1 | 12/2017 | Farritor et al. | |
| 2018/0078276 A1 * | 3/2018 | Chen | A61B 10/0266 |
| 2018/0177516 A1 | 6/2018 | Vardi et al. | |
| 2019/0336157 A1 * | 11/2019 | Ahrens | A61B 17/1608 |
| 2021/0180279 A1 * | 6/2021 | Trudeau | B23D 21/14 |

FOREIGN PATENT DOCUMENTS

| | | |
|---|---|---|
| WO | WO-2020/061181 A1 | 3/2020 |
| WO | WO-2020/061190 A1 | 3/2020 |
| WO | WO-2020/112217 A1 | 6/2020 |

OTHER PUBLICATIONS

International Search Report from International Application No. PCT/US2019/051712, dated Dec. 3, 2019.
International Search Report from International Application No. PCT/US2019/051727, dated Dec. 6, 2019.
International Search Report from International Application No. PCT/US2019/051728, dated May 5, 2020.

* cited by examiner

DEVELOPABLE AND COLLAPSABLE EXTERNAL CUTTING OR GRIPPING MECHANISM

CROSS-REFERENCE TO RELATED APPLICATION(S)

This application is a national stage filing under 35 U.S.C. 371 of International Application No. PCT/US2019/051727, filed Sep. 18, 2019, which claims priority to, and the benefit of, U.S. Provisional Application 62/732,903, filed Sep. 18, 2018, for all subject matter common to both applications. The entire teachings of the above applications are incorporated herein by reference. International Application No. PCT/US2019/051727 was published under PCT Article 21(2) in English.

STATEMENT REGARDING FEDERALLY SPONSORED RESEARCH OR DEVELOPMENT

This invention was made with government support under NSF Award No. 1663345 awarded by the National Science Foundation. The government has certain rights in the invention.

FIELD OF THE INVENTION

The present invention relates to tools, and more specifically to actuating mechanisms disposed within hollow rods suitable for performing tasks such as cutting, gripping, and/or squeezing, objects outside the hollow rod.

BACKGROUND

Generally, in the field of tools having actuating mechanisms disposed within hollow cylindrical shafts, tubes, or rods, conventional tools often allow only one mechanism to operate at the end of the rod. This is especially the case when the inner cross-sectional areas of the hollow rods are small. For example, down-hole drilling equipment, minimally invasive surgical tools, and the like, often make use of a single tool to operate at the distal end of the shaft/tube/rod and are representative of such shaft, tube, or rod type tool implementations.

SUMMARY

There is a need for hollow rod developable actuator tools having multiple developable actuating mechanisms disposed within hollow rods having small cross-sectional areas. The present invention is directed toward further solutions to address this need, in addition to having other desirable characteristics.

In accordance with example embodiments of the present invention, a hollow rod developable actuator tool is provided. The hollow rod developable actuator tool includes a first link comprising a cylinder, a first tool mechanism, and a second tool mechanism.

The cylinder of the first link includes a first end having a first aperture, a second end having a second aperture, a wall extending between the first end and second end defining an outer circumference of the hollow rod and a central passage therethrough from the first end to the second end, and a cavity in the wall having a first joint and a second joint offset from the first joint mounted therein.

The first tool mechanism includes second link in a first plane perpendicular to the central passage comprising a first tool member, a third link in a second plane perpendicular to the central passage, and a fourth link in the second plane perpendicular to the central passage. The first tool member of the second link comprises a body having a first end and a second end, a contact area on the first end of the body, a third joint in proximity to the first end of the body, a fourth joint at the second end of the body. The third link comprises a first end pivotably connected to a first joint on the first link, a second end pivotably connected to the third joint of the second link, and a body extending between the first end and second end. The fourth link comprises a first end pivotably connected to a second joint on the first link, a second end pivotably connected to the forth joint of the second link, and a body extending between the first end and second end.

The second tool mechanism includes a fifth link in the second plane perpendicular to the central passage comprising a second tool member, a sixth link in the first plane perpendicular to the central passage, and a seventh link in the first plane perpendicular to the central passage. The second tool member of the fifth link comprises a body having a first end and a second end, a contact area on the first end of the body, a fifth joint in proximity to the first end of the body, and a sixth joint at the second end of the body. The sixth link comprises a first end pivotably connected to a second joint on the first link, a second end pivotably connected to the fifth joint of the fifth link, and a body extending between the first end and second end. The seventh link comprises a first end pivotably connected to a first joint on the first link, a second end pivotably connected to the sixth joint of the fifth link, and a body extending between the first end and second end.

The hollow rod developable actuator tool transitions from a first state wherein first tool mechanism and second tool mechanism are contained entirely inside the outer circumference of the hollow rod to a second state where the first tool mechanism and second tool mechanism pass through the cavity in the wall of the first link to extend outside the outer circumference of the hollow rod.

In accordance with aspects of the present invention, the first tool mechanism and second tool mechanism are configured to engage an object between the contact areas of the first and second tool members when in the second open state. In certain such aspects, at least one of the contact area of the first tool mechanism and the contact area of the second tool mechanism is a blade.

In accordance with aspects of the present invention, at least one of the contact area of the first tool mechanism and the contact area of the second tool mechanism is a stabilizing foot.

In accordance with aspects of the present invention, at least one of the body of the second link, the body of the third link, the body of the fourth link, the body of the fifth link, the body of the sixth link, and the body of the seventh link is curved to match the curvature of the first link making the second link, third link, fourth link, fifth link, sixth link, and seventh link flush with the outer circumference when the actuator tool is in the first state.

In accordance with aspects of the present invention, the cavity of the first link is disposed in proximity to the second end of the first link.

In accordance with aspects of the present invention, the transition from the first state to the second state is actuated by cables extending length of the cylinder of the first link.

In accordance with example embodiments of the present invention, a hollow rod developable actuator tool is provided. The hollow rod developable actuator tool includes a first link comprising an inner cylinder, a first tool mechanism having a second link and a third link, a fourth link comprising an outer cylinder, and a second tool mechanism having a fifth link and a sixth link.

The inner cylinder of the first link comprises a first end having a first aperture, a second end having a second aperture, a first wall extending between the first aperture and second aperture defining an inner circumference of the hollow rod and a central passage therethrough from first aperture to the second aperture, and a first cavity in the wall having a first joint and a second sliding joint.

The first tool mechanism includes a second link comprising a first tool member and a third link. The first tool member of the second link comprises a first end pivotably connected to the wall of the first link at the first joint, a second end having a contact area, a body extending between first end and second end, and a third joint offset from the second end of the body of the second link. The third link comprises a first end pivotably connected to the third joint of the second link, a second end pivotably connected to a fourth joint, and a body extending between the first end and second end.

The outer cylinder of the fourth link includes a first end having a first aperture, a second end having a second aperture, a second wall extending between the first end and second end defining an outer circumference of the hollow rod and a central passage therethrough from first end to the second end, and a second cavity in the second wall having the fourth joint and a fifth joint.

The second tool mechanism includes a fifth link comprising a second tool member and a sixth link. The second tool member of the fifth link comprises a first end pivotably connected to the wall of the forth link at the fifth joint, a second end having a contact area, a body extending between first end and second end, and a sixth joint offset from the second end of the body of the fifth link. The sixth link comprises a first end pivotably connected to the sliding second joint on the first link, a second end pivotably connected to the sixth joint of the fifth link, and a body extending between the first end and second end.

When the inner cylinder the first link is rotated in relation to the outer ring of the fourth link, the actuator tool transitions from a first state wherein first tool mechanism and second tool mechanism are contained within the cavities of the walls to a second state where the first tool mechanism and second tool mechanism extend outside the outer circumference of the hollow rod.

In accordance with aspects of the present invention, the first tool mechanism and second tool mechanism are configured to engage an object between the contact areas of the first and second tool mechanisms. In certain aspects, at least one of the contact area of the first tool mechanism and the contact area of the second tool mechanism is a blade.

In accordance with aspects of the present invention, at least one of the contact area of the first tool mechanism and the contact area of the second tool mechanism is a stabilizing foot.

In accordance with aspects of the present invention, the body of the second link, and the body of the fifth link are curved to match the curvature of the fourth link, and the body of the third link and the body of the sixth link are curved to match the curvature of the first link making the second link, third link, fifth link, and sixth link flush with the inner and outer circumference when the actuator tool is in the first state.

In accordance with aspects of the present invention, the cavity of the first link and the cavity of the fourth link are disposed in proximity to the second end of the first link and the second end of the fourth link.

In accordance with example embodiments of the present invention, a hollow rod developable actuator tool is provided. The hollow rod developable actuator tool includes a first link comprising an inner cylinder, a first tool mechanism having a second link and a third link, a fourth link comprising an outer cylinder, and a second tool mechanism having a fifth link and a sixth link.

The inner cylinder of the first link comprises a first end having a first aperture, a second end having a second aperture, a first wall extending between the first aperture and second aperture defining an inner circumference of the hollow rod and a central passage therethrough from first aperture to the second aperture, and a first cavity in the wall having a first joint.

The first tool mechanism includes a second link and a third link. The second link comprises a first end pivotably connected to the wall of the first link at the first joint, a second end having a contact area, a body extending between first end and second end, and a second joint offset from the second end of the body of the second link. The third link comprises a first end pivotably connected to the second joint of the second link, a second end pivotably connected to a third joint, and a body extending between the first end and second end.

The outer cylinder of the fourth link includes a first end having a first aperture, a second end having a second aperture, a second wall extending between the first end and second end defining an outer circumference of the hollow rod and a central passage therethrough from first end to the second end, and a second cavity in the second wall having the third joint.

The second tool mechanism includes a fifth link and a sixth link. The fifth link comprises a first end pivotably connected to the wall of the first link at the first joint, a second end having a contact area, a body extending between first end and second end, and a fourth joint offset from the second end of the body of the fifth link. The sixth link comprises a first end pivotably connected to the fourth joint on the fifth link, a second end pivotably connected to the third joint of the fourth link, and a body extending between the first end and second end.

When the inner cylinder the first link is rotated in relation to the outer ring of the fourth link, the actuator tool transitions from a first state wherein first tool mechanism and second tool mechanism are contained within the cavities of the walls to a second state where the first tool mechanism and second tool mechanism extend outside the outer circumference of the hollow rod.

In accordance with aspects of the present invention, at least one of the first join and the third joint may be a compliant mechanism.

In accordance with example embodiments of the present invention, a method for using a hollow rod developable actuator tool is provided. The method involves providing a hollow rod developable actuator tool; and actuating the hollow rod developable actuator tool to transitions from a first closed state to a second open state.

In accordance with aspects of the present invention, the hollow rod developable actuator tool includes a first link comprising a cylinder, a first tool mechanism, and a second tool mechanism.

In accordance with aspects of the present invention, the hollow rod developable actuator tool includes a first link comprising an inner cylinder, a first tool mechanism having a second link and a third link, a fourth link comprising an outer cylinder, and a second tool mechanism having a fifth link and a sixth link.

In accordance with aspects of the present invention, the method further includes engaging an object with contact areas of a first tool member and a second tool member.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
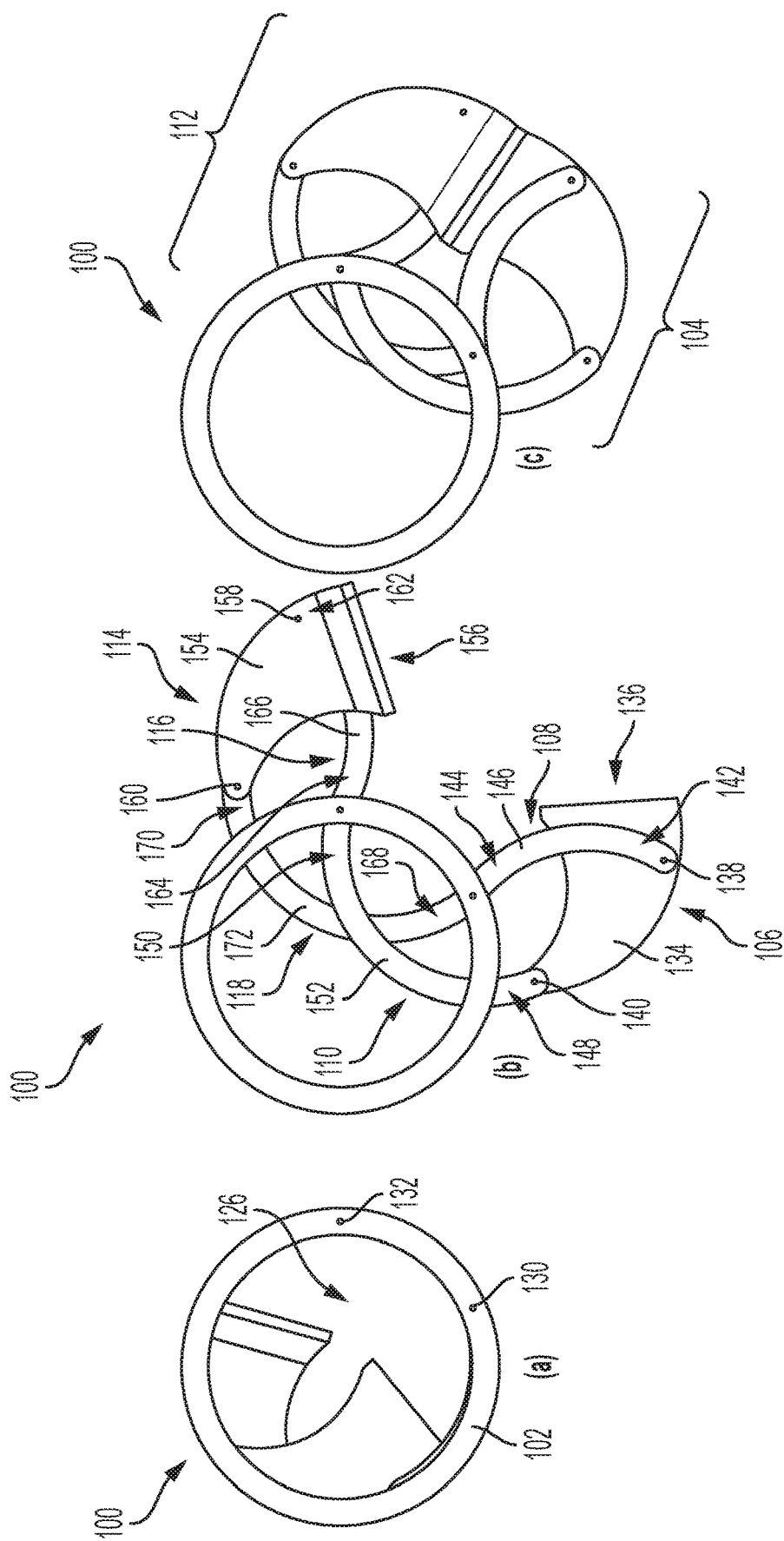
FIG. 1 shows successive illustrations of a hollow rod developable actuator tool with a central cutting and/or gripping developable actuator mechanism, the tool transitioning through different stages of actuation from stowed within the rod, to deployed open, to deployed closed.

An illustrative embodiment of the present invention relates to a hollow rod developable actuator tool. This tool includes a cylindrical tube that conceals curved-link (developable) four-bar mechanisms that can actuate to contact from two or more sides (such as to cut, grip, or squeeze) a workpiece that is outside the cylindrical tube. When the mechanism is stowed, the shaft can resemble a simple cylindrical tube with constant outer diameter. The mechanism is actuated by rotating the inner cylinder with respect to the outer cylinder, employing other rotating actuators, using actuation cables, shape memory alloys, or other actuation devices.

A single hollow rod developable actuator tool may enter a workspace through a confined entrance, while a mechanism passing through the center of the tool performs some function at the end of the hollow rod. While the mechanism is operating, it can actuate on the outside of the cylindrical tube to perform a task, such as to cut, grip, or squeeze any object on the outside of the hollow rod. This allows multiple functions to be performed with a single entry to the workspace.

Compliant components can be included in the system to make the systems bi-stable or multi-stable. Such segments can also be used put dual systems in the same plane.

FIGS. 1 through 6, wherein like parts are designated by like reference numerals throughout, illustrate an example embodiment or embodiments of a hollow rod developable actuator tool, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

As utilized herein, the term "developable" has a specific definition. A developable surface is a shape that can be made from a thin sheet of material without breaking or stretching. The term "developable mechanism" or "developable actuator" are interchangeable terms as utilized herein and describe a mechanism that conforms to or is created from a developable surface. Developable mechanisms can conform to or emerge from developable surfaces such as aircraft fuselages and wings, submarine hulls, rocket cones, and minimally invasive surgery tools.

Figure 2:
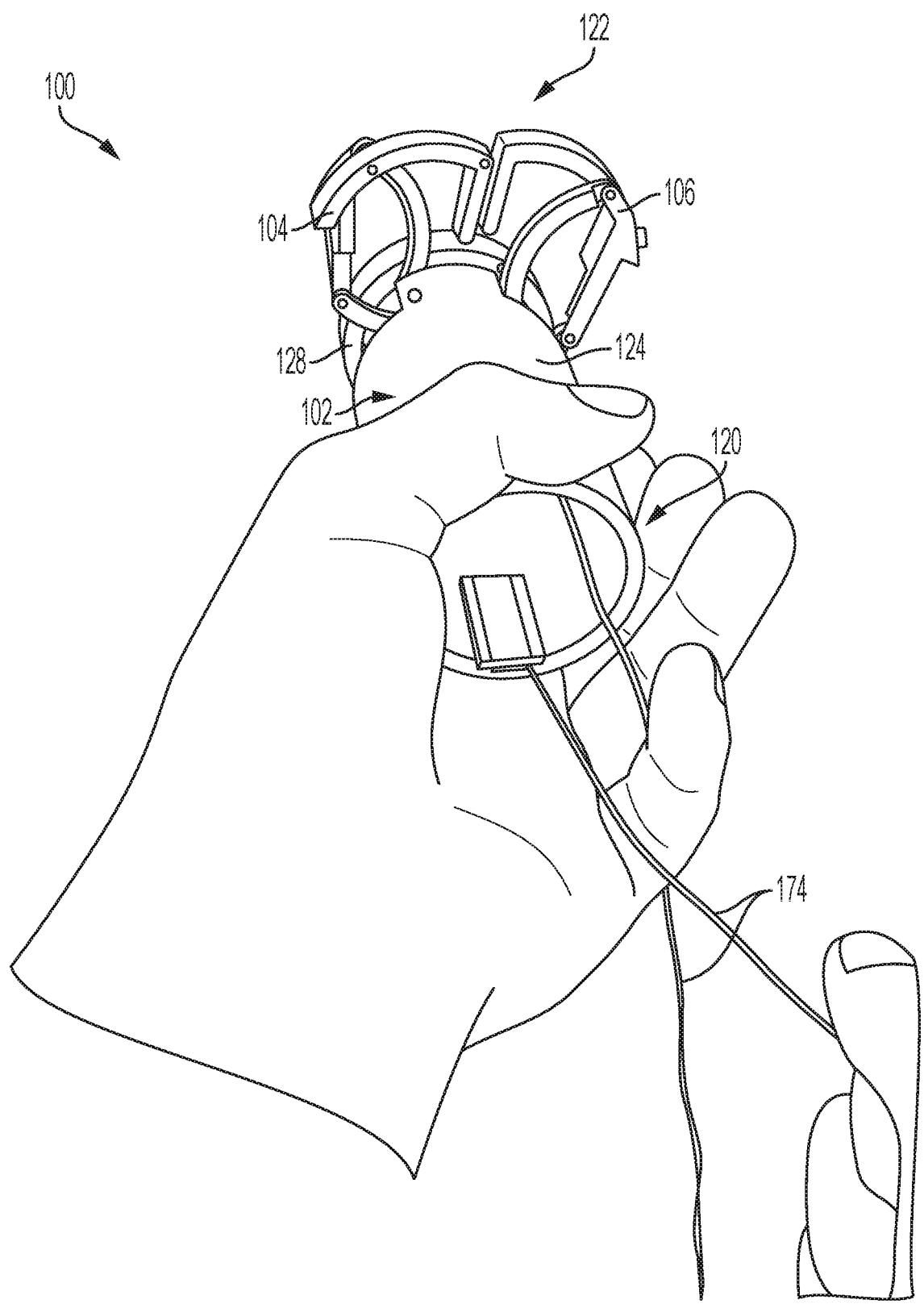
FIG. 2 is an image of the hollow rod developable actuator tool of FIG. 1 in a deployed, closed, configuration, with a pull force applied to the activation pull string.

FIG. 1 and FIG. 2 depict one embodiment of hollow rod developable actuator tool 100 of the present invention. FIG. 1 show a top down view of the hollow rod developable actuator tool 100 in successive images (a)-(c) showing the actuation of the tool from a first stowed state (a) to a second deployed state (c). FIG. 2 shows a hollow rod actuator in use. In the embodiments of FIG. 1 and FIG. 2, a single hollow rod in the form of a cylindrical hollow tube is provided with two four-bar mechanisms, both fit to the diameter and thickness of the cylinder, so that the individual links of the mechanism have the same curvature as the cylinder (although this is not a requirement for operation).

Both four-bar mechanisms share the first link 102 comprising a cylinder. The rest of the first four-bar mechanism makes up a first tool mechanism 104 including a second link 106, a third link 108, and a fourth link 110. The rest of the second four-bar mechanism makes up a second tool mechanism 112 including a fifth link 114, a sixth link 116, and a seventh link 118. Each of these elements will be described in more detail below.

The cylinder of the first link 102 has a first end 120 having a first aperture, a second end 122 having a second aperture, and a wall 124 extending between the first end 120 and second end 122 defining an outer circumference of the hollow rod developable actuator too 1100 and a central passage 126 therethrough from the first end 120 to the second end 122. A cavity 128 is disposed in the wall 124 having a first joint 130 and a second joint 132 offset from the first joint 130 mounted therein.

The wall 124 of the first link 102 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. Other suitable materials will be apparent to one skilled in the art given the benefit of this disclosure. The outer circumference of the first link 102 as well as the length of the wall 124 between the first end 120 and the second end 122 may vary depending on the intended use or application of the hollow rod developable actuator tool 100.

The cavity 128 in the wall 124 comprises a recess, cut-away, channel, passage, window, or the like that is sized and dimensioned to allow the first tool mechanism 104 and the second tool mechanism 112 to reside or otherwise be stowed in the first cavity when the mechanism of the present device is in a closed position. The first joint 130 is a pin embedded in the wall 124 and spanning the cavity 128 at one end of the cavity 128. The second joint 132 is a pin embedded in the wall 124 and spanning the cavity 128 at the other end of the cavity 128 such that the second joint 132 is offset from the first joint 130 along the circumference of the cylinder of the first link 102. Other suitable joint devices and configurations will be apparent to one skilled in the art given the benefit of this disclosure.

A discussed, the first tool mechanism 104 includes a second link 106, a third link 108, and fourth link 110. These elements in conjunction with the first link 102 make up a first four bar mechanism.

In the example of FIG. 1 and FIG. 2, the second link 106 is in a first plane perpendicular to the central passage 126 and makes up a first tool member. The first tool member of the second link 106 includes a body 134 having a first end and a second end, a contact area 136 on the first end of the body 134, a third joint 138 in proximity to the first end of the body 134, and a fourth joint 140 at the second end of the body 134.

The body 134 that makes up the first tool member of the second link 106 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 134 of the second link 106 is curved to conform to the curvature of the first link 102 such that the body 134 of the second link 106 can align with and be contained within the outer circumference of the cylinder of the first link 102 when the first tool mechanism 104 is stowed or otherwise docked in the cavity 128 in the wall 124 of the first link 102 when the mechanism is in a closed state as seen in the first image (a) of FIG. 1.

The contact area 136 is configured to engage with objects when the first tool member is extended outside the mechanism is in an open state. In certain embodiments, the contact area 136 is a gripping surface. In other embodiments, the contact area 136 is a blade. In still other embodiments, the contact area 136 is a stabilizing foot. In certain embodiments, the contact area 136 is formed as part of the body 134 from the same material as the body 134. In other embodiments, the contact area 136 can be formed of a material different from the body 134 and attached to the body 134. In certain embodiments, the contact area 136 may extend from the first plane perpendicular to the central passage 126 into the second plane perpendicular to the central passage 126. Other suitable materials and implementations will be apparent to one skilled in the art given the benefit of this disclosure.

In the example of FIG. 1 and FIG. 2, the third link 108 is in a second plane perpendicular to the central passage 126. The third link 108 has a first end 142 pivotably connected to the first joint 130 of the first link 102, a second end 144 pivotably connected to the third joint 138 of the second link 106, and a body 146 extending between the first end 142 and second end 144. The body 146 of the third link 108 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 146 of the third link 108 is curved to conform to the curvature of the first link 102 such that the body 146 of the third link 108 can reside within the cavity 128 in the first link 102 and be flush with the outer circumference of the first link 102 when the mechanism is in a closed state as seen in the first image (a) of FIG. 1.

In the example of FIG. 1 and FIG. 2, the fourth link 110 is in the second plane perpendicular to the central passage 126. The fourth link 110 has a first end 148 pivotably connected to the second joint 132 of the first link 102, a second end 150 pivotably connected to the fourth joint 140 of the second link 106, and a body 152 extending between the first end 148 and second end 150. The body 152 of the fourth link 110 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 152 of the fourth link 110 is curved to conform to the curvature of the first link 102 such that the body 152 of the fourth link 110 can reside within the cavity 128 in the first link 102 and be flush with the outer circumference of the first link 102 when the mechanism is in a closed state as seen in the first image (a) of FIG. 1.

A discussed, the second tool mechanism 112 includes a fifth link 114, a sixth link 116, and seventh link 118. These elements in conjunction with the first link 102 make up a second four bar mechanism.

In the example of FIG. 1 and FIG. 2, the fifth link 114 is in the second plane perpendicular to the central passage 126 and makes up a second tool member. The second tool member of the fifth link 114 includes a body 154 having a first end and a second end, a contact area 156 on the first end of the body 154, a fifth joint 158 in proximity to the first end of the body 154, and a sixth joint 160 at the second end of the body 154.

The body 154 that makes up the second tool member of the fifth link 114 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 154 of the fifth link 114 is curved to conform to the curvature of the first link 102 such that the body 154 of the second link 106 can align with and be contained within the outer circumference of the cylinder of the first link 102 when the second tool mechanism 112 is stowed or otherwise docked in the cavity 128 in the wall 124 of the first link 102 when the mechanism is in a closed state as seen in the first image (a) of FIG. 1.

The contact area 156 is configured to engage with objects when the second tool member is extended outside the mechanism in an open state. In certain embodiments, the contact area 156 is a gripping surface. In other embodiments, the contact area 156 is a blade. In still other embodiments, the contact area 156 is a stabilizing foot. In certain embodiments, the contact area 156 is formed as part of the body 154 from the same material as the body 154. In other embodiments, the contact area 156 can be formed of a material different from the body 154 and attached to the body 154. In certain embodiments, the contact area 156 may extend from the second plane perpendicular to the central passage 126 into the first plane perpendicular to the central passage 126. Other suitable materials and implementations will be apparent to one skilled in the art given the benefit of this disclosure.

In the example of FIG. 1 and FIG. 2, the sixth link 116 is in the first plane perpendicular to the central passage 126. The sixth link 116 has a first end 162 pivotably connected to the second joint 132 of the first link 102, a second end 164 pivotably connected to the fifth joint 158 of the fifth link 114, and a body 166 extending between the first end 162 and second end 164. The body 166 of the sixth link 116 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 166 of the sixth link 116 is curved to conform to the curvature of the first link 102 such that the body 166 of the sixth link 116 can reside within the cavity 128 in the first link 102 and be flush with the outer circumference of the first link 102 when the mechanism is in a closed state as seen in the first image (a) of FIG. 1.

In the example of FIG. 1 and FIG. 2, the seventh link 118 is in the first plane perpendicular to the central passage 126. The seventh link 118 has a first end 168 pivotably connected to the first joint 130 of the first link 102, a second end 170 pivotably connected to the sixth joint 160 of the fifth link 114, and a body 172 extending between the first end 168 and second end 170. The body 172 of the seventh link 118 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 172 of the seventh link 118 is curved to conform to the curvature of the first link 102 such that the body 172 of the seventh link 118 can reside within the cavity 128 in the first link 102 and be flush with the outer circumference of the first link 102 when the mechanism is in a closed state as seen in the first image (a) of FIG. 1.

The depth (or distance along the length of the cylinder) on the first link 102 of the first tool mechanism 104 and second tool mechanism 112 does not change the function of the mechanism. In certain embodiments, the cavity 128 of the wall 124 is located in proximity to the second end 122 of the first link 102. Thus, the first tool mechanism 104 and second tool mechanism 112 are also located in proximity to the second end 122. Typically, the first end 120 would be proximate to a user while the distal second end 122 would be inserted into the workspace.

When actuated, the tool 100 transitions from a first state wherein first tool mechanism 104 and second tool mechanism 112 are contained entirely inside the outer circumference of the cylinder of the first link 102 to a second state where the first tool mechanism 104 and second tool mechanism 112 pass through the cavity 128 in the wall 124 of the first link 102 to extend outside the outer circumference of the first link 102.

Once deployed in the second state, the first tool mechanism 104 and second tool mechanism 112 can be used to interact with an object in the environment outside the outer circumference of the tool. In certain embodiments, such as seen in FIG. 1 and FIG. 2 The first tool member of the second link 106 and the second tool member of the fifth link 114 are configured to engage an object between the contact area 136 of the second link 106 and the contact area 156 of the fifth link 114. In such embodiments, the contact areas 136, 156 can extend from the plane of their respective tool member into the plane of the corresponding tool member. Thus, the contact are 136 of the second link extends from the first plane of the first tool member into the second plane of the second tool member and the contact area 156 of the fifth link 114 extends from the second plane of the second tool member into the first plane of the first tool member. As such, the contact areas 136, 156 meet up when brought together allowing an object to be gripped between the contact areas 136, 156. In other embodiments, at least one of the contact areas 136, 156 is a blade, wherein an object is cut when the contact areas 136, 156 are brought together.

Similarly, the tool 100 can be transitioned from the second state where the first tool mechanism 104 and second tool mechanism 112 are extended outside the outer circumference of the first link 102 to the first state where the first tool mechanism 104 and second tool mechanism 112 pass through the cavity 128 in the wall 124 of the first link 102 to be contained within the cavity 128 and the outer circumference of the first link 102.

Actuation of the two four-bar mechanisms can be accomplished by the use of cables, similar to minimally invasive tools. This actuation method can be seen in FIG. 2, where cables 174 extending from the first end 120 of the cylinder of the first link 102 of the tool 100 are used to actuate the first tool mechanism 104 and second tool mechanism 112 located at the second end 122 of the cylinder of the first link 102 of the tool 100.

Figure 3:
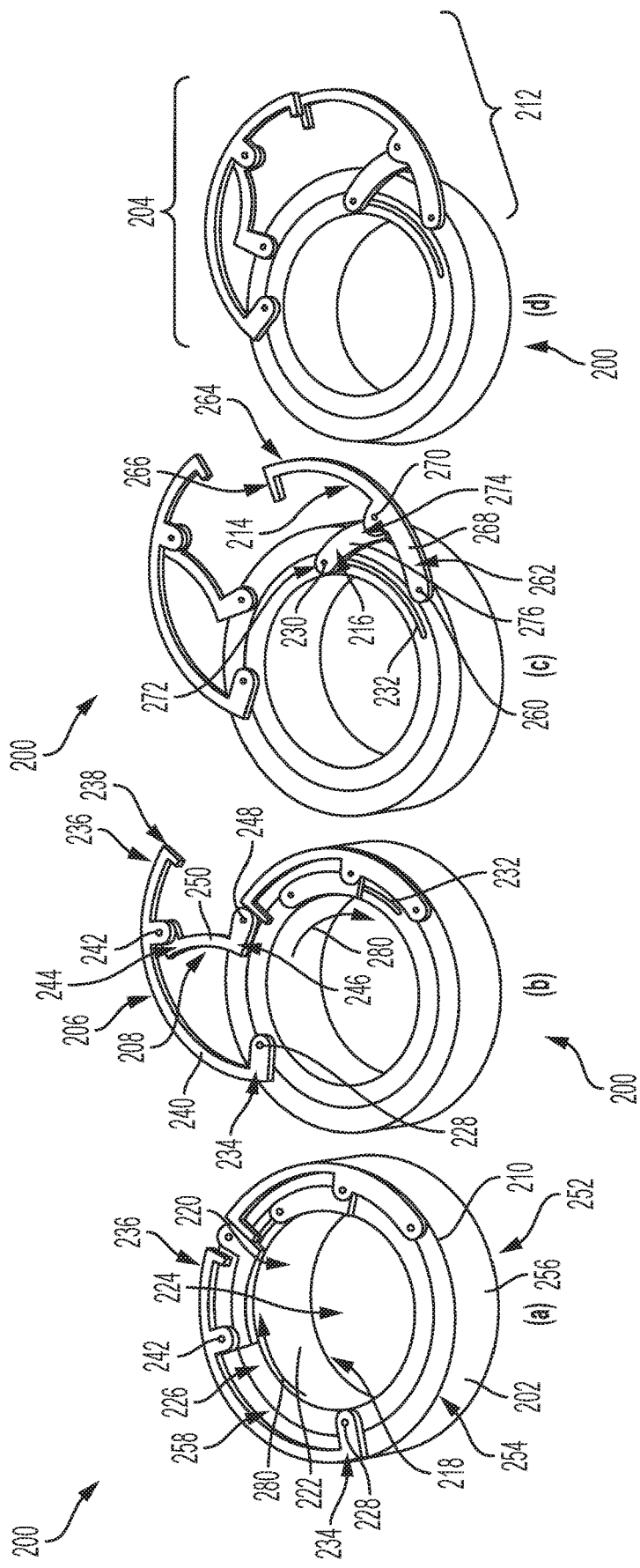
FIG. 3 shows successive isometric illustrations of a hollow rod developable actuator tool with a cutting and/or gripping developable actuator mechanism, the tool transitioning through different stages of actuation from stowed within the rod, to partially deployed, to deployed and closed.

FIG. 3 depicts another embodiment of a hollow rod developable actuator tool 200 of the present invention. FIG. 3 show a perspective view of the hollow rod developable actuator tool 200 in successive images (a)-(d) showing the actuation of the tool from a first stowed state (a) to a second deployed state (d).

In the hollow rod developable actuator tool 200 of FIG. 3, a single hollow rod in the form of a concentric cylinders is provided with two four-bar mechanisms, both fit to the diameter and thickness of the cylinder, so that the individual links of the mechanism have the same curvature as the cylinder (although this is not a requirement for operation).

A first link 202 comprising an inner cylinder is shared by both four-bar mechanisms. The first four-bar mechanism also includes a first tool mechanism 204 including a second link 206 and a third link 208. The final element of the four-bar mechanism is a fourth link 210 comprising an outer cylinder. The fourth link 210 is also shared with the second four-bar mechanism. The rest of the second four-bar mechanism makes includes second tool mechanism 212 including a fifth link 214 and a sixth link 216. Each of these elements will be described in more detail below.

The cylinder of the first link 202 has a first end 218 having a first aperture, a second end 220 having a second aperture, and a first wall 222 extending between the first end 218 and second end 220 defining an inner circumference of the tool 200 and a central passage 224 therethrough from the first end 218 to the second end 220. A first cavity 226 is disposed in the first wall 222 having a first joint 228 and a second sliding joint 230 mounted therein.

The first wall 222 of the first link 202 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. Other suitable materials will be apparent to one skilled in the art given the benefit of this disclosure. The inner circumference of the first link 202 as well as the length of the first wall 222 between the first end 218 and the second end 220 may vary depending on the intended use or application of the hollow rod developable actuator tool 200.

The first cavity 226 in the first wall 222 comprises a recess, cut-away, channel, passage, window, or the like that is sized and dimensioned to allow the first tool mechanism 204 and the second tool mechanism 212 to reside or otherwise be stowed in the first cavity 226 when the mechanism of the present device is in a stowed state. The first joint 228 is a pin embedded in the first wall 222 and spanning the first cavity 226 at one end of the first cavity 226. The sliding second joint 230 is a pin fitted in a slot 232 in the first wall 222 and spanning the first cavity 226 at the other end of the first cavity 226. Other suitable joint devices and configurations will be apparent to one skilled in the art given the benefit of this disclosure.

A discussed, the first tool mechanism 204 includes a second link 206 and a third link 208. These elements in conjunction with the first link 202 and the fourth link 210 make up a first four bar mechanism.

In the example of FIG. 3, the second link 206 makes up a first tool member. The first tool member of the second link 206 includes a first end 234 pivotably connected to the first wall 222 of the first link 202 at the first joint 228, a second end 236 having a contact area 238, a body 240 extending between the first end 234 and second end 236, and a third joint 242 offset from the second end 236 of the second link 206.

The body 240 that makes up the first tool member of the second link 206 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 240 of the second link 206 is curved to conform to the curvature of the first link 202 such that the body 240 of the second link 206 can align with and be contained within the outer circumference of the cylinder of the fourth link 210 when the first tool mechanism 204 is in a stowed state as seen in the first image (a) of FIG. 3.

The contact area 238 is configured to engage with objects when the first tool member is extended outside the mechanism is in a deployed state. In certain embodiments, the contact area 238 is a gripping surface. In other embodiments, the contact area 238 is a blade. In still other embodiments, the contact area 238 is a stabilizing foot. In certain embodiments, the contact area 238 is formed as part of the body 240 from the same material as the body 240. In other embodiments, the contact area 238 can be formed of a material different from the body 240 and attached to the body 240. Other suitable materials and implementations will be apparent to one skilled in the art given the benefit of this disclosure.

The third link 208 has a first end 244 pivotably connected to the third joint 242 of the second link 206, a second end 246 pivotably connected to a fourth joint 248, and a body 250 extending between the first end 244 and second end 246. The body 250 of the third link 208 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 250 of the third link 208 is curved to conform to the curvature of the first link 202 such that the body 250 of the third link 208 can reside within the first cavity 226 in the first link 202 and be flush with the inner circumference of the first link 202 when the mechanism is in a stowed state as seen in the first image (a) of FIG. 3.

The outer cylinder of the fourth link 210 has a first end 252 having a first aperture, a second end 254 having a second aperture, and a second wall 256 extending between the first end 252 and the second end 254 defining an outer circumference of the hollow rod and the central passage 224 therethrough from the first end 252 to the second end 254. A second cavity 258 is disposed in the second wall 256 having the fourth joint 248 mounted and a fifth joint 260 mounted therein.

The second wall 256 of the fourth link 210 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. Other suitable materials will be apparent to one skilled in the art given the benefit of this disclosure. The outer circumference of the fourth link 210 as well as the length of the second wall 256 between the first end 252 and the second end 254 may vary depending on the intended use or application of the hollow rod developable actuator tool 200.

The second cavity 258 in the second wall 256 comprises a recess, cut-away, channel, passage, window, or the like that is sized and dimensioned to allow the first tool mechanism 204 the second tool mechanism 212 to reside or otherwise be stowed in the second cavity 258 when the mechanism of the present device is in a closed position. In the embodiment of FIG. 3 the fourth joint 248 is a pin embedded in the second wall 256 and spanning the second cavity 258 located at one end of the second cavity 258. The fifth joint 260 is a pin embedded in the second wall 256 and spanning the second cavity 258 at the other end of the second cavity 258. Other suitable joint devices or mechanism will be apparent to one skilled in the art given the benefit of this disclosure.

A discussed, the second tool mechanism 212 includes a fifth link 214 and a sixth link 216. These elements in conjunction with the first link 202 and the fourth link 210 make up the second four-bar mechanism.

In the example of FIG. 3, the fifth link 214 makes up a second tool member. The second tool member of the fifth link 214 includes a first end 262 pivotably connected to the second wall 256 of the fourth link 210 at the fifth joint 260, a second end 264 having a contact area 266, a body 268 extending between the first end 262 and second end 264, and a sixth joint 270 offset from the second end 264 of the fifth link 214.

The body 268 that makes up the second tool member of the fifth link 214 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 268 of the fifth link 214 is curved to conform to the curvature of the fourth link 210 such that the body 268 of the fifth link 214 can align with and be contained within the outer circumference of the cylinder of the fourth link 210 when the second tool mechanism 212 is in a stowed state as seen in the first image (a) of FIG. 3.

The contact area 266 is configured to engage with objects when the second tool member is extended outside the mechanism in a deployed state. In certain embodiments, the contact area 266 is a gripping surface. In other embodiments, the contact area 266 is a blade. In still other embodiments, the contact area 266 is a stabilizing foot. In certain embodiments, the contact area 266 is formed as part of the body 268 from the same material as the body 268. In other embodiments, the contact area 266 can be formed of a material different from the body 268 and attached to the body 268. Other suitable materials and implementations will be apparent to one skilled in the art given the benefit of this disclosure.

The sixth link 216 has a first end 272 pivotably connected to the sliding second joint 230 of the first link 202, a second end 274 pivotably connected to a sixth joint 270 of the fifth link 214, and a body 276 extending between the first end 272 and second end 274. The body 276 of the sixth link 216 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 250 of the sixth link 216 is curved to conform to the curvature of the first link 202 such that the body 250 of the sixth link 216 can reside within the first cavity 226 in the first link 202 and be flush with the inner circumference of the first link 202 when the mechanism is in a stowed state as seen in the first image (a) of FIG. 3.

The depth (or distance along the length of the cylinder) on the fourth link 210 of the first link 202, first tool mechanism 204, and second tool mechanism 212 does not change the function of the mechanism. In certain embodiments, the first link 202 extends the full length of the fourth link. In certain embodiments, the first cavity 226 of the first wall 222 and the second cavity 258 of the second wall 256 are located in proximity to the second end 254 of the fourth link 210 and the second end 220 of the first link 202. Thus, the first tool mechanism 204 and second tool mechanism 212 are also located proximity to the second ends 220, 254. Typically, the first ends 218,252 would be proximate to a user while the distal second ends 220, 254 would be inserted into the workspace.

When the inner cylinder of the first link 202 is rotated in relation to the outer cylinder of the fourth link 210 such as indicated by arrow 280, the tool 200 transitions from a first state wherein first tool mechanism 204 and second tool mechanism 212 are contained within the first cavity 226 of the first wall 222 of the first link 202 and the second cavity 258 of the second wall 256 of the fourth link 210 as seen in the first image (a) of FIG. 3 to a second state where the first tool mechanism 204 and second tool mechanism 212 pass through the second cavity 258 in the second wall 256 of the fourth link 210 to extend outside the outer circumference of the fourth link 210 where the first tool mechanism 204 and second tool mechanism 212 can interact with an object outside the tool 200 as seen in the last image (d) of FIG. 3. In the second image (b) of FIG. 3 the first tool mechanism 204 is extended at the inner cylinder of the first link 202 is rotated in relation to the outer cylinder of the fourth link 210 as indicated by arrow 280 moving the first joint 228 on the first link 202 toward the fourth joint 248 on the fourth link 210 swinging the third link 208 outward which in turn moves the first tool member of the second link 206 outside the tool 200. The pin of sliding second join 230 sliding through slot 232 prevents the second tool mechanism 212 from being deployed. In the third image (c) of FIG. 3, the pin of the sliding second joint 230 reaches the end of the slot 232 and the sixth link 216 swings outward which in turn moves the second tool member of the fifth link 214 outside the tool 200. In the final image (d) of FIG. 3 the first tool mechanism 204 and second tool mechanism 212 are in the extended in the second deployed state.

Once deployed in the second state, the first tool mechanism 204 and second tool mechanism 212 can be used to interact with an object in the environment outside the outer circumference of the tool. In certain embodiments, such as seen in FIG. 3, the first tool member of the second link 206 and the second tool member of the fifth link 214 are configured to engage an object between the contact area 238 of the second link 206 and the contact area 266 of the fifth link 214.

Similarly, the tool 200 can be transitioned from the second state where the first tool mechanism 204 and second tool mechanism 212 are extended outside the outer circumference of the fourth link 210 to the first state where the first tool mechanism 204 and second tool mechanism 212 pass through the second cavity 258 in the second wall 256 of the fourth link 210 to be contained within the inner and outer circumferences of the tool 200. This is achieved by rotating the inner cylinder of the first link 202 in relation to the outer cylinder of the fourth link 210 in the reverse direction that was used to actuate the tool 200.

Figure 4A:
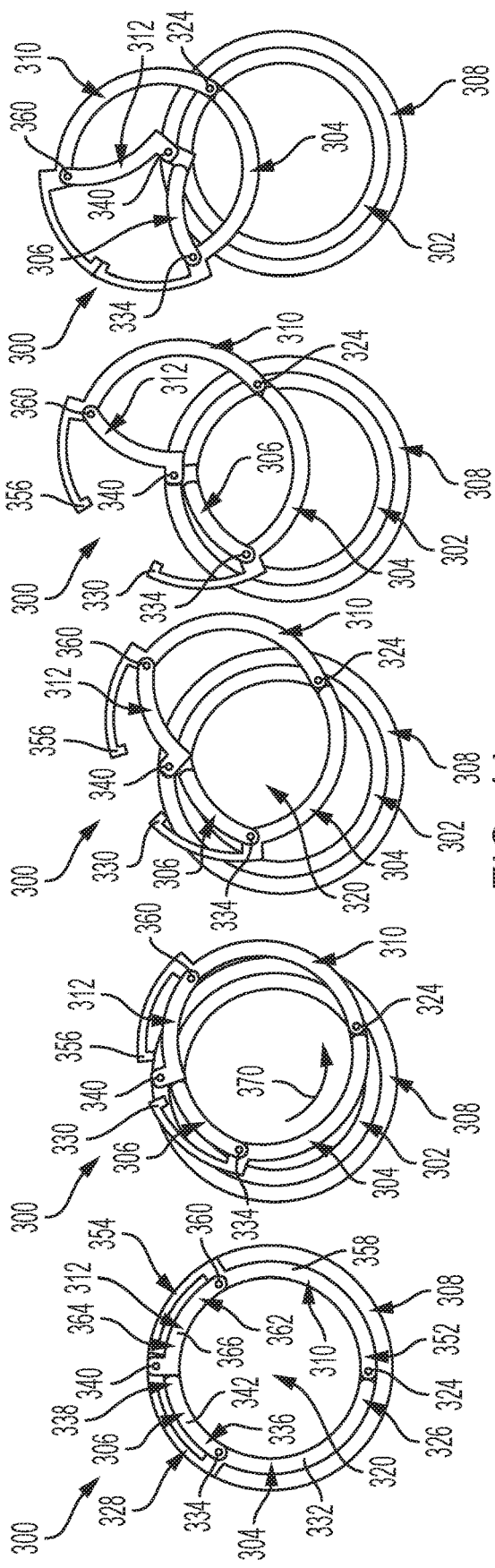
FIG. 4A shows successive illustrations of a hollow rod developable actuator tool with a cutting and/or gripping developable actuator mechanism, the tool transitioning through different stages of actuation from stowed within the rod, to partially deployed, to deployed and closed.
Figure 4B:
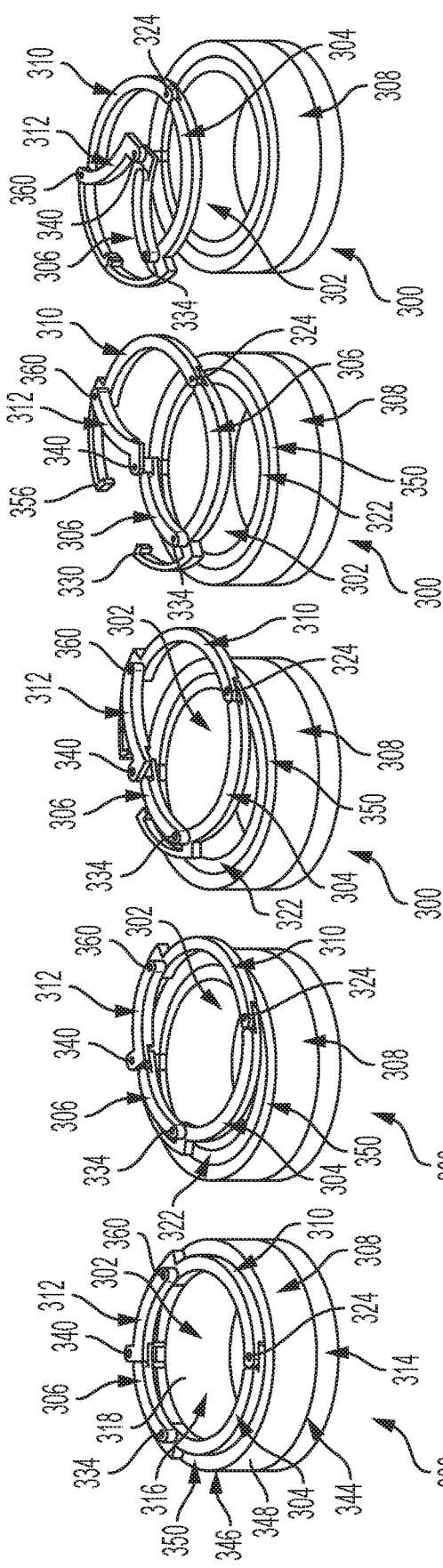
FIG. 4B shows successive illustrations of the hollow rod developable actuator tool of FIG. 4A with a cutting and/or gripping developable actuator mechanism, the tool transitioning through different stages of actuation from stowed within the rod, to partially deployed, to deployed and closed.
Figure 4C:
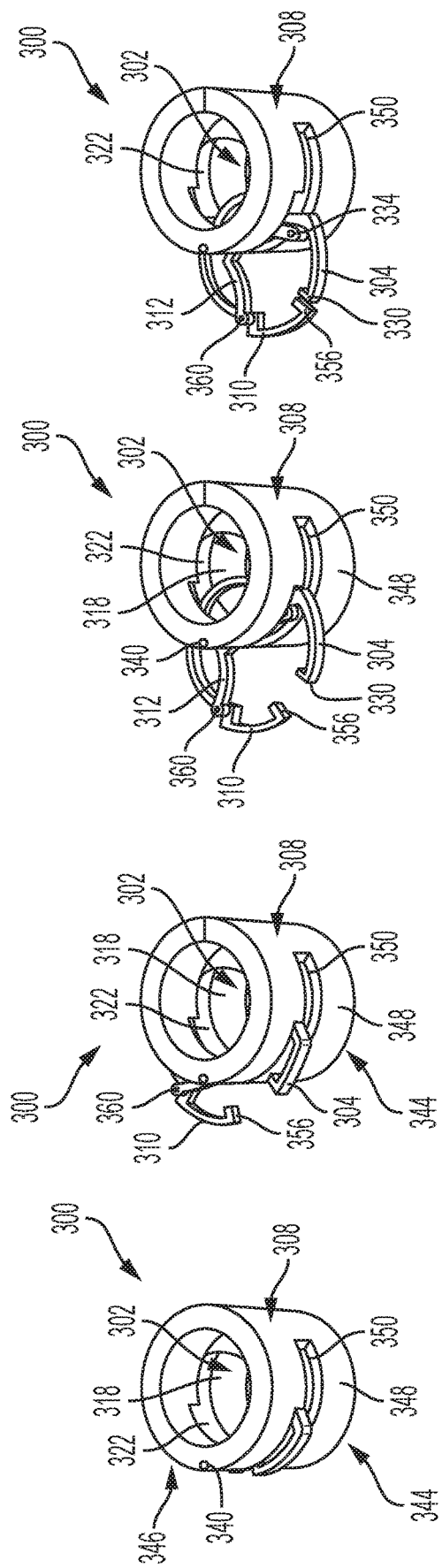
FIG. 4C shows successive perspective illustrations of a hollow rod developable actuator tool with a cutting and/or gripping developable actuator mechanism using compliant mechanisms, the tool transitioning through different stages of actuation from stowed within the rod, to partially deployed, to deployed and closed.

In accordance with another embodiment of the present invention, and turning to FIGS. 4A through 4C, two four-bar mechanisms share two common joints located on two concentric cylinders. Actuation is achieved by the rotation of the inner cylinder and the mechanism. These features allow for the gripping surfaces to meet at two different locations based on the direction of rotation.

FIG. 4A and FIG. 4B depicts another embodiment of a hollow rod developable actuator tool 400 of the present invention. FIG. 4A show a top-down view of the hollow rod developable actuator tool 300 in successive images showing the actuation of the tool 300 from a first stowed state to a second deployed state. FIG. 4B shows an isometric view of the hollow rod developable actuator tool 300 in successive images.

In the hollow rod developable actuator tool 200 of FIG. 4A and FIG. 4B, a single hollow rod in the form of a concentric cylinders is provided with two four-bar mechanisms, both fit to the diameter and thickness of the cylinder, so that the individual links of the mechanism have the same curvature as the cylinder (although this is not a requirement for operation).

A first link 302 comprising an inner cylinder is shared by both four-bar mechanisms. The first four-bar mechanism also includes a first tool mechanism including a second link 304 and a third link 306. The final element of the four-bar mechanism is a fourth link 308 comprising an outer cylinder. The fourth link 308 is also shared with the second four-bar mechanism. The rest of the second four-bar mechanism is second tool mechanism including a fifth link 310 and a sixth link 312. Each of these elements will be described in more detail below.

The cylinder of the first link 302 has a first end 314 having a first aperture, a second end 316 having a second aperture, and a first wall 318 extending between the first end 314 and second end 316 defining an inner circumference of the tool 300 and a central passage 320 therethrough from the first end 314 to the second end 316. A first cavity 322 is disposed in the first wall 318 having a first joint 324 mounted therein.

The first wall 318 of the first link 302 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. Other suitable materials will be apparent to one skilled in the art given the benefit of this disclosure. The inner circumference of the first link 302 as well as the length of the first wall 318 between the first end 314 and the second end 416 may vary depending on the intended use or application of the hollow rod developable actuator tool 300.

The first cavity 322 in the first wall 318 comprises a recess, cut-away, channel, passage, window, or the like that is sized and dimensioned to allow the second link 304 and third link 306 of the first tool mechanism as well as the fifth link 310 and sixth link of the second tool mechanism to reside or otherwise be stowed in the first cavity 322 when the mechanism of the present device is in a stowed state. The first joint 324 is a pin embedded in the first wall 318 and spanning the first cavity 322. Other suitable joint devices and configurations will be apparent to one skilled in the art given the benefit of this disclosure.

A discussed, the first tool mechanism includes a second link 304 and a third link 306. These elements in conjunction with the first link 302 and the fourth link 308 make up a first four bar mechanism.

The second link 304 includes a first end 326 pivotably connected to the first wall 318 of the first link 302 at the first joint 324, a second end 328 having a contact area 330, a body 332 extending between the first end 326 and second end 328, and a second joint 334 offset from the second end 328 of the second link 304.

The body 332 of the second link 304 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 332 of the second link 304 is curved to conform to the curvature of the first link 302 such that the body 332 of the second link 304 can align with and be contained within the outer circumference of the cylinder of the fourth link 308 when the tool 300 is in a stowed state as seen in the left-most images of FIG. 4A and FIG. 4B.

The contact area 330 is configured to engage with objects when the first tool mechanism is extended outside the mechanism is in a deployed state. In certain embodiments, the contact area 330 is a gripping surface. In other embodiments, the contact area 330 is a blade. In still other embodiments, the contact area 330 is a stabilizing foot. In certain embodiments, the contact area 330 is formed as part of the body 332 from the same material as the body 332. In other embodiments, the contact area 330 can be formed of a material different from the body 332 and attached to the body 332. Other suitable materials and implementations will be apparent to one skilled in the art given the benefit of this disclosure.

The third link 306 has a first end 336 pivotably connected to the second joint 334 of the second link 304, a second end 338 pivotably connected to a third joint 340, and a body 342 extending between the first end 336 and second end 338. The body 342 of the third link 306 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 342 of the third link 306 is curved to conform to the curvature of the first link 302 such that the body 342 of the third link 306 can reside within the first cavity 322 in the first link 302 and be flush with the inner circumference of the first link 302 when the mechanism is in a stowed state as seen in the left-most images of FIG. 4A and FIG. 4B.

The outer cylinder of the fourth link 308 has a first end 344 having a first aperture, a second end 346 having a second aperture, and a second wall 348 extending between the first end 344 and the second end 346 defining an outer circumference of the hollow rod and the central passage 320 therethrough from the first end 344 to the second end 346. A second cavity 350 is disposed in the second wall 348 having the third joint 340 mounted therein.

The second wall 348 of the fourth link 308 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. Other suitable materials will be apparent to one skilled in the art given the benefit of this disclosure. The outer circumference of the fourth link 308 as well as the length of the second wall 348 between the first end 344 and the second end 346 may vary depending on the intended use or application of the hollow rod developable actuator tool 300.

The second cavity 350 in the second wall 348 comprises a recess, cut-away, channel, passage, window, or the like that is sized and dimensioned to allow the second link 304 and third link 306 of the first tool mechanism and the fifth link 310 and sixth link 312 of the second tool mechanism to reside or otherwise be stowed in the second cavity 350 when the mechanism of the present device is in a closed position. In the embodiment of FIG. 4A and FIG. 4B the third joint 340 is a pin embedded in the second wall 348 and spanning the second cavity 350. Other suitable joint devices or mechanism will be apparent to one skilled in the art given the benefit of this disclosure.

A discussed, the second tool mechanism includes a fifth link 310 and a sixth link 312. These elements in conjunction with the first link 302 and the fourth link 308 make up the second four-bar mechanism. In addition, the fifth link 310 shares the first joint 324 with the second link 304 and the sixth link 312 shares the third joint 340 with the third link 306.

The fifth link 310 includes a first end 352 pivotably connected to the first wall 318 of the first link 302 at the first joint 324, a second end 354 having a contact area 356, a body 358 extending between the first end 352 and second end 354, and a fourth joint 360 offset from the second end 354 of the fifth link 310.

The body 358 that makes up the second tool member of the fifth link 310 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 358 of the fifth link 310 is curved to conform to the curvature of the fourth link 308 such that the body 358 of the fifth link 310 can align with and be contained within the outer circumference of the cylinder of the fourth link 308 when the second tool mechanism is in a stowed state as seen in the left-most images of FIG. 4A and FIG. 4B.

The contact area 356 is configured to engage with objects when the second tool mechanism is extended outside the tool 300 in a deployed state. In certain embodiments, the contact area 356 is a gripping surface. In other embodiments, the contact area 356 is a blade. In still other embodiments, the contact area 356 is a stabilizing foot. In certain embodiments, the contact area 356 is formed as part of the body 358 from the same material as the body 358. In other embodiments, the contact area 356 can be formed of a material different from the body 358 and attached to the body 358. Other suitable materials and implementations will be apparent to one skilled in the art given the benefit of this disclosure.

The sixth link 312 has a first end 362 pivotably connected to the fourth joint 360 of the fifth link 310, a second end 364 pivotably connected to a third joint 340 of the fourth link 308, and a body 366 extending between the first end 362 and second end 364. The body 366 of the sixth link 312 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 366 of the sixth link 312 is curved to conform to the curvature of the first link 302 such that the body 366 of the sixth link 312 can reside within the first cavity 322 in the first link 302 and be flush with the inner circumference of the first link 302 when the mechanism is in a stowed state as seen in the left-most images of FIG. 4A and FIG. 4B The depth (or distance along the length of the cylinder) on the fourth link 308 of the first link 302, first tool mechanism, and second tool mechanism does not change the function of the mechanisms. In certain embodiments, the first link 302 extends the full length of the fourth link 308. In certain embodiments, the first cavity 322 of the first wall 318 and the second cavity 350 of the second wall 348 are located in proximity to the second end 346 of the fourth link 308 and the second end 316 of the first link 302. Thus, the first tool mechanism and second tool mechanism are also located in proximity to the second ends 316, 346. Typically, the first ends 314,344 would be proximate to a user while the distal second ends 316, 346 would be inserted into the workspace.

When the inner cylinder of the first link 302 is rotated in relation to the outer cylinder of the fourth link 308 such as indicated by arrow 370, the tool 300 transitions from a first state wherein the second link 304 and third link 306 of the first tool mechanism and the fifth link 310 and sixth link 312 of the second tool mechanism are contained within the first cavity 322 of the first wall 318 of the first link 302 and the second cavity 350 of the second wall 348 of the fourth link 308 as seen in the left-most images of FIG. 4A and FIG. 4B to a second state where the second link 304 and third link 306 of the first tool mechanism and the fifth link 310 and sixth link 312 of the second tool mechanism pass through the second cavity 350 in the second wall 348 of the fourth link 308 to extend outside the outer circumference of the fourth link 308 where the contact area 330 of the second link 304 and the contact area 356 of the firth link 310 can interact with an object outside the tool 300 as seen in the right-most images of FIG. 4A and FIG. 4B. Once deployed in the second state, the first tool mechanism 204 and second tool mechanism 212 can be used to interact with an object in the environment outside the outer circumference of the tool.

Similarly, the tool 300 can be transitioned from the second state where the second link 304 and third link 306 of the first tool mechanism and the fifth link 310 and sixth link 312 of the second tool mechanism are extended outside the outer circumference of the fourth link 308 to the first state where the second link 304 and third link 306 of the first tool mechanism and the fifth link 310 and sixth link 312 of the second tool mechanism pass through the second cavity 350 in the second wall 348 of the fourth link 308 to be contained within the inner and outer circumferences of the tool 300. This is achieved by rotating the inner cylinder of the first link 302 in relation to the outer cylinder of the fourth link 308 in the reverse direction that was used to actuate the tool 300.

In certain embodiments is it possible to further simplify the manufacture, assembly, and overall complexity of the tool 300 through the use of compliant mechanism. By applying principles of compliant mechanisms, the pin joints can be replaced by compliant segments and provide the same motion. FIG. 4C shows a compliant version of the mechanism illustrated in FIG. 4A and FIG. 4B. These compliant configurations allow for more manufacturing methods such as planar CNC routing and die cutting.

FIG. 4C shows a perspective view of the hollow rod developable actuator tool 300 in successive images. The left-most image shows the tool in a closed or stowed state while the right-most image shows the tool 300 in a open or deployed state.

In this embodiment, one or more of the shared first joint 324 or shared third joint 340 is replaced with a compliant mechanism. The compliant mechanism take advantage of the flexible nature of the materials forming the joint to allow to material to flex replicating the degree of motion provided by the conventional pin joint. By using compliant mechanisms, the second link 304 and fifth link 310 can be formed of one piece of material. In a similar manner, the third link 306 and sixth link 312 and also be formed of one piece of material.

The two mechanisms share one single piece, and through the compliance of the piece, achieve motion similar to two separate links. The compliance also makes the system bistable.

It is stressed that the shape of the links is arbitrary for mechanism motion. As long as the distance between the pins remains the same and the links do not self-interfere, the mechanism will have the same motion. To completely conceal the moving links when the mechanism is closed, the links are constrained to a radius of curvature of the cylindrical tube of the hollow rod and to a shape that will fit inside the hollow rod when fully collapsed.

Figure 5A:
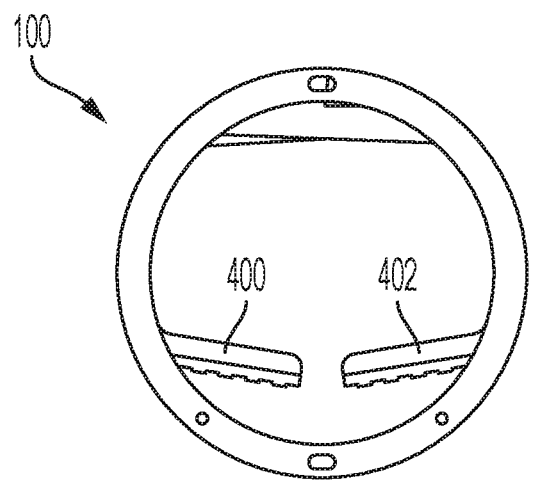
FIGS. 5A and 5B show a hollow rod developable actuator tool in a stowed state and then in a fully deployed state, the tool directed toward a non-gripping application, such as using the mechanism as a landing gear or stabilizing feet for the cylindrical tube.
Figure 5B:
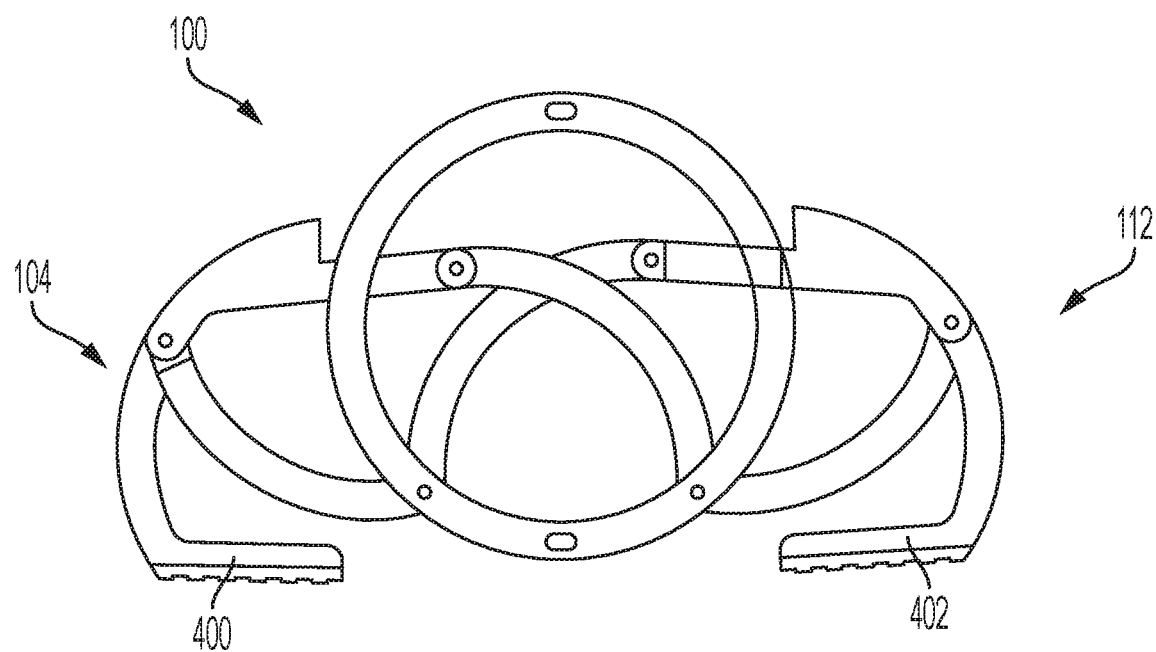

As mentioned previously, in certain embodiments, the contact areas 136, 156, 238, 266 of the first tool mechanisms 104, 204 and second tool mechanisms 112, 212 are configured as stabilizing feet. FIGS. 5A and 5B show a non-gripping application, such as using the first tool mechanisms 104, 204 and second tool mechanism 112, 212 as a landing gear or stabilizing feet for the tool 100, 200. FIG. 5A shows the tool 100 of FIG. 1 and FIG. 2 where contact areas 136, 156 are configured as stabilizing feet 400, 402 and are in a first stowed state. FIG. 5B shows the tool 100 wherein the stabilizing feet 400, 402 and are in a second deployed state.

Figure 6:
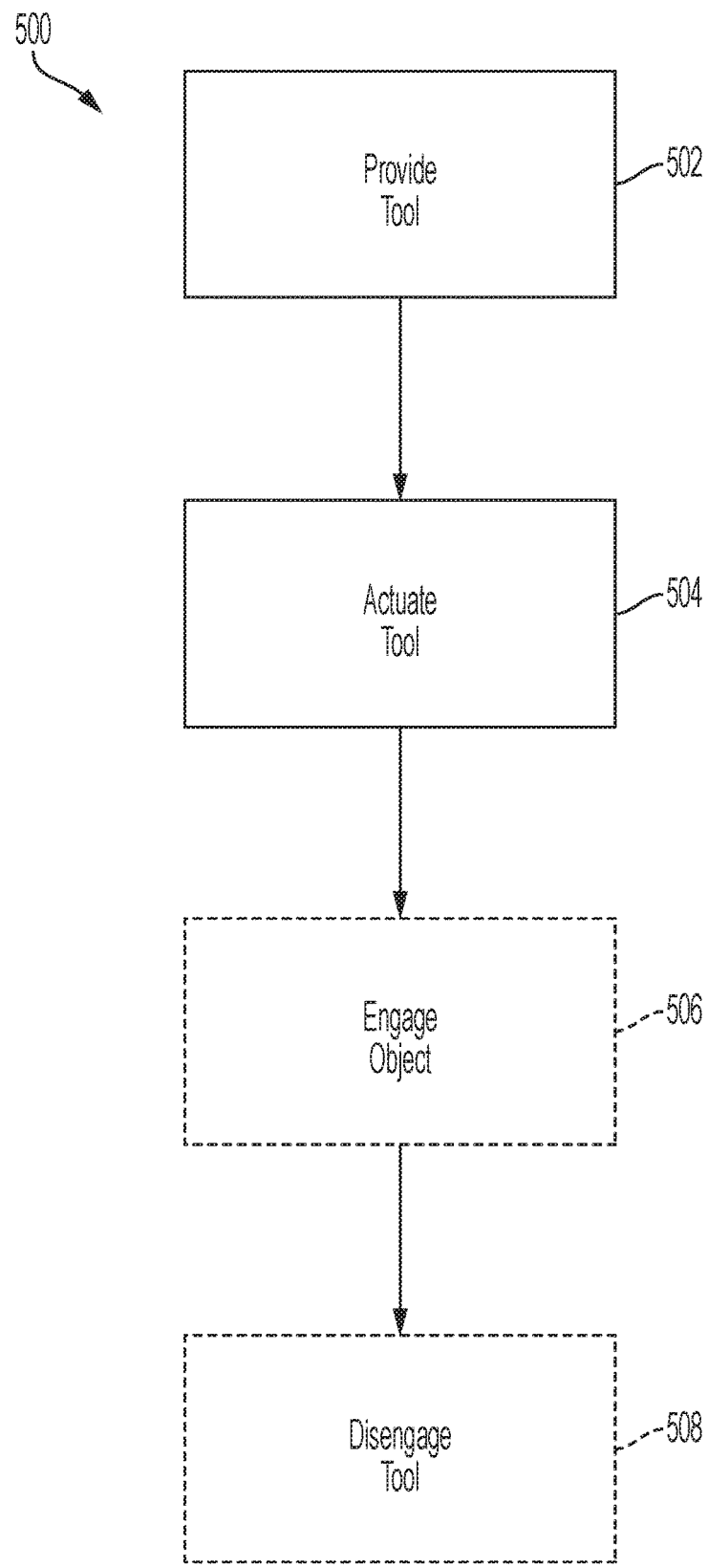
FIG. 6 is a flow diagram of a methodology for using a hollow rod developable actuator tool.

FIG. 6 depicts a methodology 500 for using the hollow rod developable actuator tools 100, 200 of the present invention. First a hollow rod developable actuator tool 100, 200 as described herein is provided (Step 502). This tool 100, 200 can be deployed in the particular workspace where hollow rod actuator tools are typically used such as drill site or surgical environment. The tool 100, 200 can then be actuated in the workspace (Step 504) to transition from a first closed state to a second open state wherein the mechanism can be used to interact with an item in the outside the circumference of the tool 100, 200 (step 506). In certain embodiments, the tool 100, 200 may also be transitioned from the second open state back to the first closed state to disengage the tool 100, 200 (Step 508) wherein the tool 100 can be withdrawn from the workspace.

The actuating of the tool 100, 200 (step 504) is shown in the successive images of FIG. 1 and FIG. 3 moving left to right with the left-most image being the tool 100, 200 in a first stowed state and the right most image being the tool 100 in a deployed second state wherein the tool 100, 200 engages an object in the outside the circumference of the tool 100, 200.

In the embodiment of FIG. 1 and FIG. 2, the tool 100 is actuated through the use of actuation cables 174 shown in FIG. 2. In the embodiment of FIG. 3, the tool 200 is actuated by rotating the inner cylinder of the first link 202 in relation to the outer cylinder of the fourth link 210.

In some embodiments, the engagement of an object (step 506) by the contact areas 136, 238 of the first tool mechanism 104, 204 and the contact area 156, 266 of the second tool mechanism 112, 212 involves grasping the object between the contact areas 136, 238 of the first tool mechanism 104, 204 and the contact area 156, 266 of the second tool mechanism 112, 212. In other embodiments, such as when at least one of the contact areas 136, 156, 238, 266 are a blade, the engagement of an object by the contact areas 136, 238 of the first tool mechanism 104, 204 and the contact area 156, 266 of the second tool mechanism 112, 212 involves cutting the object between the contact areas 136, 238 of the first tool mechanism 104, 204 and the contact area 156, 266 of the second tool mechanism 112, 212. In still other embodiments, such as seen in FIG. 5A and FIG. 5B, the contact areas 136, 156 stabilizing feet 400, 402 that when deployed, served to stabilize, balance or otherwise situate the tool 100 on the object.

In a similar manner, the tool 100, 200 can be disengaged (step 508), by transitioning the tool 100, 200 from the deployed second state to the first stowed state. At such time, the tool 100, 200 can be withdrawn from the environment.

Conventional cylindrical shaft or tube tools often allow only one tool to operate at the end of the shaft, especially when the tubes are small. The present invention enables an instrument or mechanism to be included in the cylindrical tube and to enter a workspace through a single entrance in combination with other instruments on the end of the shaft. This can i) lower the time required to perform a task in a confined/remote workspace by reducing the number of tooling changes required; ii) reduce the trauma/damage to the boundary of the workspace by reducing the number of entrance holes/points required; iii) reduce trauma/damage to the workspace by limiting interface between the blades/grippers and body tissue, since the only tissue interacting with the blades/grippers is that which is drawn into the inner diameter of the cylindrical shaft; iv) reduce the complexity of the control system used in conjunction with the tooling setup, as fewer shafts would be required to enter the space, and v) reduce the cost of the procedure.

To any extent utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A hollow rod developable actuator tool, the tool comprising:
   a first link comprising a cylinder comprising:
      a first end having a first aperture;
      a second end having a second aperture;
      a wall extending between the first end and second end defining an outer circumference of the hollow rod and a central passage therethrough from the first end to the second end; and
      a cavity in the wall having a first joint and a second joint offset from the first joint mounted therein;
   a first tool mechanism comprising:
      second link in a first plane perpendicular to the central passage comprising a first tool member, the first tool member comprising:
         a body having a first end and a second end;
         a contact area on the first end of the body;
         a third joint in proximity to the first end of the body; and
         a fourth joint at the second end of the body;
      a third link in a second plane perpendicular to the central passage, the third link comprising:
         a first end pivotably connected to a first joint on the first link;
         a second end pivotably connected to the third joint of the second link; and
         a body extending between the first end and second end; and
      a fourth link in the second plane perpendicular to the central passage, the fourth link comprising:
         a first end pivotably connected to a second joint on the first link;
         a second end pivotably connected to the forth joint of the second link; and
         a body extending between the first end and second end;
   a second tool mechanism comprising:
      a fifth link in the second plane perpendicular to the central passage comprising a second tool member, the second tool member comprising:
         a body having a first end and a second end;
         a contact area on the first end of the body;
         a fifth joint in proximity to the first end of the body; and
         a sixth joint at the second end of the body;
      a sixth link in the first plane perpendicular to the central passage, the sixth link comprising:
         a first end pivotably connected to a second joint on the first link;
         a second end pivotably connected to the fifth joint of the fifth link; and
         a body extending between the first end and second end; and
      a seventh link in the first plane perpendicular to the central passage, the seventh link comprising:
         a first end pivotably connected to a first joint on the first link;
         a second end pivotably connected to the sixth joint of the fifth link; and
         a body extending between the first end and second end;
   wherein, the actuator tool transitions from a first state wherein first tool mechanism and second tool mechanism are contained entirely inside the outer circumference of the hollow rod to a second state where the first tool mechanism and second tool mechanism pass through the cavity in the wall of the first link to extend outside the outer circumference of the hollow rod.

2. The hollow rod developable actuator tool of claim 1, wherein the first tool mechanism and second tool mechanism engage an object between the contact area of the first and second tool members.

3. The hollow rod developable actuator tool of claim 2, wherein at least one of the contact area of the first tool mechanism and the contact area of the second tool mechanism is a blade.

4. The hollow rod developable actuator tool of claim 1, wherein at least one of the contact area of the first tool mechanism and the contact area of the second tool mechanism is a stabilizing foot.

5. The hollow rod developable actuator tool of claim 1, wherein at least one of the body of the second link, the body of the third link, the body of the fourth link, the body of the fifth link, the body of the sixth link, and the body of the seventh link is curved to match the curvature of the first link making the second link, third link, fourth link, fifth link, sixth link, and seventh link flush with the outer circumference when the actuator tool is in the first state.

6. The hollow rod developable actuator tool of claim 1, wherein the cavity of the first link is disposed in proximity to the second end of the first link.

7. The hollow rod developable actuator of claim 1, wherein the transition from the first state to the second state is actuated by cables extending the length of the cylinder of the first link.

8. A hollow rod developable actuator tool, the tool comprising:
   a first link comprising an inner cylinder, the inner cylinder comprising:
      a first end having a first aperture;
      a second end having a second aperture;
      a first wall extending between the first end and second end defining an inner circumference of the hollow rod and a central passage therethrough from first end to the second end; and
      a first cavity in the first wall having a first joint and a second sliding joint;
   a first tool mechanism comprising:
      a second link comprising a first tool member, the first tool member comprising:
         a first end pivotably connected to the wall of the first link at the first joint;
         a second end having a contact area;
         a body extending between first end and second end; and
         a third joint offset from the second end of the body of the second link;
      a third link comprising:
         a first end pivotably connected to the third joint of the second link;
         a second end pivotably connected to a fourth joint; and
         a body extending between the first end and second end;

a fourth link comprising an outer cylinder, the outer cylinder comprising:
  a first end having a first aperture;
  a second end having a second aperture,
  a second wall extending between the first end and second end defining an outer circumference of the hollow rod and a central passage therethrough from first end to the second end; and
  a second cavity in the second wall having the fourth joint and a fifth joint;
a second tool mechanism comprising:
  a fifth link comprising a second tool member, the second tool member comprising:
    a first end pivotably connected to the wall of the forth link at the fifth joint;
    a second end having a contact area;
    a body extending between first end and second end; and
    a sixth joint offset from the second end of the body of the fifth link; and
  a sixth link comprising:
    a first end pivotably connected to the sliding second joint on the first link;
    a second end pivotably connected to the sixth joint of the fifth link; and
    a body extending between the first end and second end;
wherein, when the inner cylinder the first link is rotated in relation to the outer ring of the fourth link, the actuator tool transitions from a first state wherein first tool mechanism and second tool mechanism are contained within the cavities of the walls to a second state where the first tool mechanism and second tool mechanism extend outside the outer circumference of the hollow rod.

9. The hollow rod developable actuator tool of claim 8, wherein the first tool mechanism and second tool mechanism are configured to engage an object between the contact areas of the first and second tool mechanisms.

10. The hollow rod developable actuator tool of claim 9, wherein at least one of the contact area of the first tool mechanism and the contact area of the second tool mechanism is a blade.

11. The hollow rod developable actuator tool of claim 8, wherein at least one of the contact area of the first tool mechanism and the contact area of the second tool mechanism is a stabilizing foot.

12. The hollow rod developable actuator tool of claim 8, wherein of the body of the second link, and the body of the fifth link are curved to match the curvature of the fourth link, and the body of the third link and the body of the sixth link are curved to match the curvature of the first link making the second link, third link, fifth link, and sixth link flush with the inner and outer circumference when the actuator tool is in the first state.

13. The hollow rod developable actuator tool of claim 8, wherein the cavity of the first link and the cavity of the fourth link are disposed in proximity to the second end of the first link and the second end of the fourth link.

14. A hollow rod developable actuator tool, the tool comprising:
a first link comprising an inner cylinder, the inner cylinder comprising:
  a first end having a first aperture;
  a second end having a second aperture;
  a first wall extending between the first end and second end defining an inner circumference of the hollow rod and a central passage therethrough from first end to the second end; and
  a first cavity in the first wall having a first joint;
a first tool mechanism comprising:
  a second link comprising:
    a first end pivotably connected to the wall of the first link at the first joint;
    a second end having a contact area;
    a body extending between first end and second end; and
    a second joint offset from the second end of the body of the second link;
  a third link comprising:
    a first end pivotably connected to the second joint of the second link;
    a second end pivotably connected to a third joint; and
    a body extending between the first end and second end;
a fourth link comprising an outer cylinder, the outer cylinder comprising:
  a first end having a first aperture;
  a second end having a second aperture,
  a second wall extending between the first end and second end defining an outer circumference of the hollow rod and a central passage therethrough from first end to the second end; and
  a second cavity in the second wall having the third joint;
a second tool mechanism comprising:
  a fifth link comprising:
    a first end pivotably connected to the wall of the first link at the first joint;
    a second end having a contact area;
    a body extending between first end and second end; and
    a fourth joint offset from the second end of the body of the fifth link; and
  a sixth link comprising:
    a first end pivotably connected to the fourth joint on the fifth link;
    a second end pivotably connected to the third joint of the fourth link; and
    a body extending between the first end and second end;
wherein, when the inner cylinder the first link is rotated in relation to the outer ring of the fourth link, the actuator tool transitions from a first state wherein first tool mechanism and second tool mechanism are contained within the cavities of the walls to a second state where the first tool mechanism and second tool mechanism extend outside the outer circumference of the hollow rod.

15. The hollow rod developable actuator tool of claim 14, wherein the first tool mechanism and second tool mechanism are configured to engage an object between the contact areas of the first and second tool mechanisms.

16. The hollow rod developable actuator tool of claim 15, wherein at least one of the contact area of the first tool mechanism and the contact area of the second tool mechanism is a blade.

17. The hollow rod developable actuator tool of claim 14, wherein at least one of the contact area of the first tool mechanism and the contact area of the second tool mechanism is a stabilizing foot.

18. The hollow rod developable actuator tool of claim 14, wherein of the body of the second link, and the body of the fifth link are curved to match the curvature of the fourth link, and the body of the third link and the body of the sixth link are curved to match the curvature of the first link making the second link, third link, fifth link, and sixth link flush with the inner and outer circumference when the actuator tool is in the first state.

19. The hollow rod developable actuator tool of claim 14, wherein the cavity of the first link and the cavity of the fourth link are disposed in proximity to the second end of the first link and the second end of the fourth link.

20. The hollow rod developable actuator tool of claim 14, wherein at least one of the first joint and the third joint is s compliant mechanism.

* * * * *